(12) United States Patent
Brunner

(10) Patent No.: US 10,329,588 B2
(45) Date of Patent: Jun. 25, 2019

(54) DEVICE FOR THE BIOMETHANATION OF $H_2$ AND $CO_2$

(71) Applicant: Matthias Brunner, Saarbruecken (DE)

(72) Inventor: Matthias Brunner, Saarbruecken (DE)

( * ) Notice: Subject to any disclaimer, the term of this patent is extended or adjusted under 35 U.S.C. 154(b) by 0 days.

(21) Appl. No.: 14/901,585

(22) PCT Filed: Jun. 27, 2014

(86) PCT No.: PCT/EP2014/063719
§ 371 (c)(1),
(2) Date: Dec. 28, 2015

(87) PCT Pub. No.: WO2014/207211
PCT Pub. Date: Dec. 31, 2014

(65) Prior Publication Data
US 2016/0369303 A1    Dec. 22, 2016

(30) Foreign Application Priority Data

Jun. 28, 2013 (DE) .................. 10 2013 010 826

(51) Int. Cl.
*C12M 1/00* (2006.01)
*C12M 1/06* (2006.01)
(Continued)

(52) U.S. Cl.
CPC ............. *C12P 5/023* (2013.01); *C12M 21/04* (2013.01); *C12M 23/58* (2013.01); *C12M 25/14* (2013.01);
(Continued)

(58) Field of Classification Search
CPC ...... C12M 23/58; C12M 29/24; C12M 27/02; C12M 25/14; C12M 29/06; C12M 21/04; C12P 5/023; Y02E 50/343
See application file for complete search history.

(56) References Cited

U.S. PATENT DOCUMENTS

2009/0130734 A1    5/2009  Mets
2011/0177558 A1*   7/2011  Medoff et al. ......... C12M 21/12
                                                                435/72
2013/0005010 A1    1/2013  Bell et al.

FOREIGN PATENT DOCUMENTS

EP          1 574 581        9/2005
JP            06169783        6/1994
KR      10-2009-0008987      1/2009

OTHER PUBLICATIONS

Guiot et al., "Potential of Wastewater-Treating Anaerobic Granules for Biomethanation of Synthesis Gas," Environ. Sci. Technol., 2011, 45:2006-2012.

* cited by examiner

*Primary Examiner* — Gautam Prakash
(74) *Attorney, Agent, or Firm* — Riverside Law LLP

(57) ABSTRACT

The invention relates to means and methods for the biomethanation of $H_2$ and $CO_2$. In particular, the invention relates to devices for producing methane by means of methanogenic microorganisms by converting $H_2$ and $CO_2$, wherein the devices comprise at least one reactor, an aqueous medium, which is provided in the at least one reactor, wherein the methanogenic microorganisms are contained in the aqueous medium, a feeding apparatus, which is designed to introduce $H_2$ and $CO_2$ into the at least one reactor, wherein $H_2$ and $CO_2$ form a gaseous mixture therein, and a reaction-increasing device, which is designed to enlarge the contact surface between the aqueous medium having the methanogenic microorganisms and the gaseous mixture. The invention further relates to methods for producing methane in a reactor device by means of methanogenic microorganisms.

19 Claims, 5 Drawing Sheets

(51) Int. Cl.
 *C12M 1/12* (2006.01)
 *C12P 5/02* (2006.01)
 *C12M 1/107* (2006.01)

(52) U.S. Cl.
 CPC ............ *C12M 27/02* (2013.01); *C12M 29/06* (2013.01); *C12M 29/24* (2013.01); *Y02E 50/343* (2013.01)

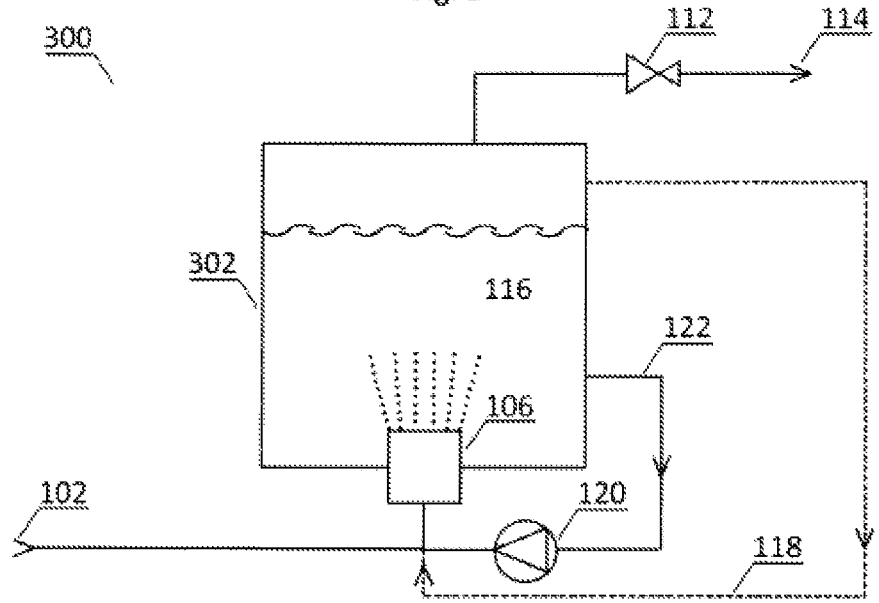
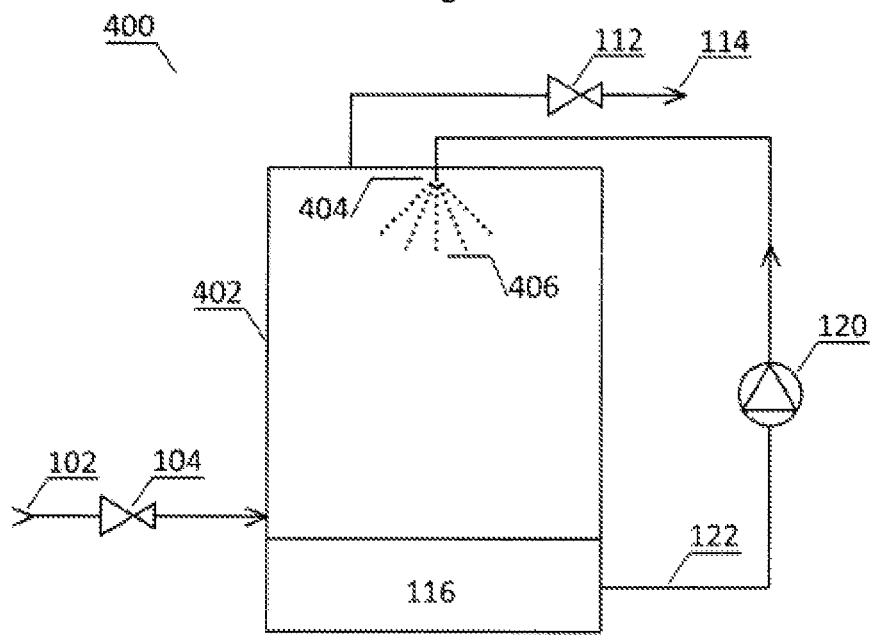

DEVICE FOR THE BIOMETHANATION OF $H_2$ AND $CO_2$

CROSS-REFERENCE TO RELATED APPLICATIONS

This application is the U.S. national phase application filed under 35 U.S.C. § 371 claiming benefit to International Patent Application No. PCT/EP14/063719, filed Jun. 27, 2014, which is entitled to priority under 35 U.S.C. § 119 (a)-(d) to DE application no. 10-2013-010826.8, filed Jun. 28, 2013, each of which application is hereby incorporated herein by reference in its entirety.

BACKGROUND OF THE INVENTION

A storage of energy is possible according to the "power to gas" concept by creating storable methane. First of all, hydrogen is generated with unused peaks of regeneratively produced energy by electrolysis. From hydrogen ($H_2$) together with carbon dioxide ($CO_2$) storable methane ($CH_4$) can be produced. The methane formation can be written by the following equation: $4H_2+CO_2 \Leftrightarrow CH_4+2H_2O$ (so-called Sabatier reaction). This reaction can be carried out in a purely chemical and in a biological way. The chemical reaction is constrained at temperatures above 180° C. and high pressures and is make possible by relatively demanding catalysts.

The biological transformation occurs by special microorganisms. In natural, anaerobic, aqueous ecosystems such as marshes, sewage sludge or flooded soil, consortia of several groups of organisms form methane through a chain of decomposition from organic material such as plant and animal remains. There are mesophilic consortia and thermophilic consortia. Their temperature optima lie at 30-40° C. and 50-60° C., respectively. The methane bacteria form the last link in this chain of decomposition, which break down organic substrate through many intermediate steps such as organic acids, alcohols and hydrogen, into methane and carbon dioxide. Methane bacteria are among the Archaebacteria (Archaea). They live only under oxygen-free conditions, have very specific nutrient requirements, grow very slowly and have a very restricted substrate spectrum. Some methane bacteria utilize acetic acid or formic acid to form methane. Other methane bacteria form methane by the above equation from hydrogen and carbon dioxide.

The known technical layouts for biogenic methane formation are not suited to the conversion of gaseous substrates. Such layouts as biogas plants, digestion towers, or plants for anaerobic sludge treatment have been optimized exclusively to biomethanize hydrolyzable or dissolved organic substrates via the mentioned chains of decomposition. Hydrogen is also formed as an intermediate product. It needs a very low hydrogen partial pressure of less than $10^{-4}$ bar in order to further break down the resulting organic intermediate products. Hydrogen consuming methane bacteria maintain the necessary low hydrogen partial pressure. If hydrogen were added to this process, the entire decomposition chain could be damaged and brought to a standstill.

If methane is to be produced with the above described hydrogen-utilizing bacteria, the highest possible hydrogen partial pressure should prevail, unlike the case of the above chain of decomposition, in order to supply the bacteria with their gaseous substrate. The groups of organisms upstream from the methane bacteria in the chain of decomposition then no longer play any role. Thus, more gas should be supplied than the bacteria are able to convert, in order to achieve a maximum conversion rate.

Pure cultures of such organisms are supplied with their substrates directly via the gas phase for research purposes on the laboratory scale (reagent glasses, flasks, etc.). The organisms draw in the gases metabolized by them from the gas phase by a gradient and give off the methane formed to the gas phase. Such pure cultures are not used on an industrial scale, since being strict anaerobes they are killed by even traces of oxygen. Thus far, neither was there any incentive to use them. The organisms need to be supplied with gas in a different way on an industrial scale.

Given this background, and as part of new energy storage concepts (power to gas), methods have been proposed to use methane bacteria for conversion of hydrogen and carbon dioxide that are designed to increase the gas exchange surface: solid bed reactors with large gas phase. Suitable organisms grow here as biofilms on substrate materials, being flushed with nutritive medium and supplied from the gas phase. The drawback of these methods is that these surfaces first need to be overgrown by the organisms. But methane bacteria grow very slowly and even under optimal conditions they have generation times of several days. Furthermore, it is questionable how methane bacteria could even form a biofilm. The startup phase of such reactors is very long in practice, uncertain, and hardly controllable. If the biofilms later become too thick, the organisms in the interior can only be supplied suboptimally and "dead zones" will result. The biomass concentration per reactor volume can thus only be controlled with difficulty. After an injury to the organisms by a malfunction, such reactors can only slowly be placed back in operation. There is no known use of these methods in practice.

In summary, it can be said that the generation and storage of SNG (Substitute Natural Gas) in the natural gas grid represents a highly promising option for storing energy from renewable sources by making use of the existing natural gas infrastructure and operating with high efficiencies. But there is still a need to optimize the methane gas production.

The problem which the present invention proposes to solve is therefore to provide effective and economical means and methods with which methane can be produced by making use of methanogenic microorganisms.

SUMMARY OF THE INVENTION

This problem is solved by the present invention; in particular, the problem is solved by the following aspects of the present invention, such as devices, methods, or uses and embodiments thereof, as well as the subject matter of the claims. The figures illustrate the present invention.

In a first aspect, the present invention concerns a device for the production of methane by means of methanogenic microorganisms through conversion of $H_2$ and $CO_2$, having:
- at least one reactor;
- an aqueous medium, which is prepared in the at least one reactor, the methanogenic microorganisms being located in the aqueous medium;
- a feed mechanism, which is designed to channel $H_2$ and $CO_2$ into the at least one reactor, where the $H_2$ and $CO_2$ form a gaseous mixture inside it;
- a reaction boosting device, which is designed to increase the contact surface between the aqueous medium with the methanogenic microorganisms and the gaseous mixture.

In a second aspect, the present invention concerns the use of a device according to the invention for the production of methane by means of methanogenic microorganisms by conversion of $H_2$ and $CO_2$.

In a third aspect, the invention concerns methods for production of methane in a reactor device according to the invention by means of methanogenic microorganisms, which are located in the reactor device in an aqueous medium, by conversion of $H_2$ and $CO_2$ as the reaction gas mixture, characterized in that the contact surface between the aqueous medium with the methanogenic microorganisms and the gaseous mixture is increased by means of a reaction boosting device during the conversion.

The present invention thus concerns devices, methods or uses and embodiments thereof, which are described in detail below. Preferred embodiments which are described, e.g., for devices, also apply mutatis mutandis to methods or uses, and conversely, i.e., embodiments which are described e.g. for methods or uses also apply mutatis mutandis to devices.

Methane ($CH_4$) can be created chemically and microbially from hydrogen ($H_2$) and carbon dioxide ($CO_2$). The chemical reaction occurs catalytically at over 180° C. and high pressure. Accordingly, there are high demands on the material and equipment. Microbially, $H_2$ and $CO_2$ are metabolized in aquatic ecosystems by methane bacteria under physiological conditions to produce $CH_4$. These organisms can also be used industrially. Known layouts for biomethanization (biogas plants etc.) are only suitable for the decomposition of solid or dissolved organic carbon compounds. Adding $H_2$ has disrupted this decomposition. Industrial layouts for the microbial conversion of $H_2$ and $CO_2$ are not known. The supply of $H_2$ limits the metabolism of the bacteria. On a laboratory scale, submerse reactors are known, as well as anaerobic filter with surfaces overgrown by bacteria. Methane bacteria, however, populate such surfaces very slowly.

The inventor has now discovered that an effective and economical way of producing methane gas in reactors, preferably solid state reactors, is possible, contrary to the view of the prior art, as long as the methanogenic microorganisms are brought ideally into contact with the substrates hydrogen ($H_2$) and carbon dioxide ($CO_2$). For this, the inventor proposes increasing in suitable manner, ideally maximizing, the contact surface between the aqueous medium of the reactor in which the methanogenic microorganisms are located and the gaseous substrate gas mixture (gaseous mixture). For example, and preferably, the contact surface between the aqueous medium in the reactor of the device according to the invention and the gaseous mixture containing carbon dioxide and hydrogen is increased by means of a reaction boosting device.

To increase the contact surface it has been proposed in the prior art to let methanogenic microorganisms grow in the form of a biofilm and in a solid bed, such as one placed as a filler body in a reactor, and then to flush them with $H_2$ and $CO_2$ while a liquid film is running or trickling over the microorganisms located in the biofilm (DE 10 2011 051 836). With this design, one wished to do without the hydrostatic liquid column that is established in a reactor, because it was assumed that this hinders the introducing of the substrate gases $H_2$ and $CO_2$ or has the effect that $CO_2$ in particular is dissolved in the aqueous medium of the reactor and thus is not available as substrate gas for the methanogenic microorganisms. However, it was misunderstood that a biofilm of methanogenic microorganisms could even be formed, let alone how long it would take for such a biofilm to arise, so that a corresponding device for the production of methane by means of methanogenic microorganisms could be operated cheaply and effectively. Typically, methanogenic microorganisms even under ideal conditions have a generation time of 3-5 days. Furthermore, there cannot be any entry of oxygen either in the growth phase or later on during a possible reactor shutdown, since the methanogenic microorganisms are strictly anaerobic and would be killed off at once. A shutdown of the device would not be unusual, since it is entirely customary in the power to gas project, for example, that current is only used during peak times to split water electrolytically into hydrogen and oxygen ($O_2$) in order to convert the resulting hydrogen together with carbon dioxide into methane by means of methanogenic microorganisms. That is, a device of this kind, even the device according to the invention, can easily have lengthy down times, e.g., if current is not be converted into gas (here, methane) on account of a heavy demand. However, the device described in DE 10 2011 051 836 would be unsuitable for such instances, since the biofilm would not survive unless flushed constantly with aqueous medium. Furthermore, it is exposed defenseless to an incursion of oxygen, and the methanogenic microorganisms would die off at once.

The device according to the invention does not have these drawbacks. Even though the crux of the invention is also based on increasing the contact surface between the methanogenic microorganism and the gaseous mixture containing carbon dioxide and hydrogen, this is preferably not done by means of biofilm formation and/or by growth of the methanogenic microorganisms in a solid bed, substrate or matrix.

The device according to the invention therefore preferably has a reaction boosting device for increasing the contact surface between the aqueous medium with the methanogenic microorganisms and the gaseous mixture containing hydrogen and carbon dioxide, which does not increase the contact surface by immobilization of methanogenic microorganisms on the surface of filler bodies and/or not by sprinkling the filler bodies with the methanogenic microorganisms immobilized on them and/or not by channeling gaseous substrates over the methanogenic microorganisms immobilized on the surface of filler bodies.

In the sample embodiments described for the device for production of methane by means of methanogenic microorganisms the reaction boosting device works on the aqueous medium containing the methanogenic microorganisms such that its surface in contact with the substrate gas is increased. The reaction boosting device can be a body with a very large ratio of surface to volume, such as a body with a honeycomb or perforated structure, and this surface is accessible to both the aqueous medium and the substrate gas from the outside. The increasing of the reaction surface by means of the reaction boosting device can be done for example by supplying energy by means of mechanically dynamic means such as nozzles, stirrers, and the like, by means of mechanically static means such as screens or seepage arrays, or also by means of a mixture of these two means. The reaction boosting device can be set up to produce a turbulent mixing or stirring of the aqueous medium with the substrate gas. At the same time or in addition, the reaction boosting device can be set up to distribute one of the fluids, i.e., the aqueous medium or the substrate gas, within the other fluid as discrete particles (such as gas particles or liquid particles), so that the contact surface between the two fluids is drastically increased and in a first approximation of the sum of the surfaces of the fluid converted to particles. As examples one can mention here the introducing of the substrate gas into the aqueous medium by means of a driving jet nozzle, wherein the substrate gas forms fine gas bubbles (seen here as gas particles) and can be distributed in the aqueous medium, or the atomization or dispersion of the aqueous medium (into tiny particles of liquid) into a volume containing the substrate gas.

Furthermore, one preferred embodiment of the present invention is that the methanogenic microorganisms are not immobilized in the aqueous medium of the reactor of the device according to the invention. This is accomplished, e.g., in that mechanical or pneumatic energy is constantly introduced into the reactor, e.g., by flowing or formation of gas bubbles in the reactor. In this way, the methanogenic microorganisms cannot form any biofilm. Likewise, it is provided that no specific opportunity of forming a biofilm is provided to the methanogenic microorganisms, such as by providing surface structures in the form of a matrix or a surface structure suitable for the formation of a biofilm.

Since the device according to the invention is suitable to accommodate microorganisms, especially methanogenic microorganisms, by means of which methane is produced, the device according to the invention will often also be called here a "bioreactor".

The reactor of the device according to the invention is set up as a stationary or nonstationary reactor in one preferred embodiment. The reactor is preferably a solid state reactor.

Solid state reactors (Solid State Fermentation-Bioreactors; SFB) are reactors which are used for the cultivation of microorganisms and for industrial production of, e.g., enzymes, drugs, and nutrients. In the present case, for the production of methane. One distinguishes between stationary and nonstationary solid state reactors. The stationary reactors include, among others, Petri dishes, Fernbach flasks, wooden incubators, the covered pan bioreactor as well as column SSF (Solid State Fermentation, SSF) bioreactors. The nonstationary reactors include the rotary drum SFB, the stirred SFB and the tumbling SFB.

The reactor of a device according to the invention can be set up as a continuous ideal stirred tank reactor (CSTR), a discontinuous ideal stirred tank reactor (STR), a tube reactor, a loop reactor, reactors hooked up in series, or a cascade of reactors (cascade reactor or stirred tank cascade).

Each reactor contains the three phases of solid (biomass), liquid (nutritive medium) and gaseous. In the reactor according to the invention, their distribution is maintained by various measures, such as movable mechanical installed parts (stirrers): for example, in the stirred tank reactor, external pump circuit: the liquid is recirculated by a pump, e.g., free jet reactor, blowing in of gas: the gas phase is blown into the liquid component, e.g., airlift reactor or bubble column reactor. Since the crux of the invention is to bring the methanogenic microorganisms as optimally as possible into contact with the gaseous mixture, containing $CO_2$ and $H_2$, the aspect of blowing in the gaseous mixture is of special significance for the present invention. Therefore, the airlift reactor or bubble column reactor is a preferred embodiment of the reactor of the device according to the invention.

Besides the simple bubble column, so-called loop reactors (bubble columns with internal and external circuit of the liquid) are also used in a preferred embodiment according to the invention. They consist of a bubble column, in which an internal tube is placed coaxially. The gas is blown into the liquid via a nozzle or frit so that a bubble column is formed in the inner tube. The loop reactor is used as a back-mixing reactor in cases of liquid reaction mixtures of high viscosity. In this, the reaction mass is back-mixed by looplike partial returns in a tube reactor system.

The loop reactors can be subdivided as follows, all of the subdivisions being preferred embodiments of the present invention: jet loop reactor and outflow loop reactor.

A jet loop reactor is characterized by a homogeneous distribution of gas and liquid. In the jet loop reactor, the liquid in a driving jet is directed at the reactor bottom so that it can seize and break up the gas. Examples of jet loop reactors are the Mammut loop reactor or the jet loop reactor. An outflow loop reactor is characterized by very large gas dwell times, which can be set up at low structural height. It is used in the conversion of rather small specific gas quantities.

If loop reactors are provided with baffle pipes, one gets the following reactor types: propeller loop reactor (a reactor in which energy is inserted through an axially downward delivery stirrer, being provided with a baffle pipe), jet loop reactor (a free jet reactor with a baffle pipe), Mammut loop reactor (an airlift reactor or a bubble column reactor with a baffle pipe).

In one preferred embodiment, the reactor of the device according to the invention is set up as a submerse reactor. In a submerse reactor according to the invention, the gas/liquid exchange surface is maintained by dispersal of the gas phase in the liquid. Energy is constantly imported: either pneumatically, e.g., gasification; mechanically, e.g., by stirrers or by forced convection of the liquid, e.g., liquid pump in an external circuit.

The embodiment as a submerse reactor stands in contrast to the teaching of DE 10 2011 051 836, which advises against submerse reactors and gives preference to biofilm reactors. But this misses the point that, contrary to the customary operation of bioreactors, it is possible to recirculate bacteria constantly with the gas mixture containing $H_2$ and $CO_2$ in the aqueous medium, or even saturate them with the gas mixture. This is accomplished, e.g., in that the gas mixture thanks to the importing of mechanical or pneumatic energy is supplied permanently and in large quantity to the aqueous medium. The methanogenic microorganisms are always in motion and are permanently surrounded by the gas mixture, so that they always have an opportunity to take up $CO_2$ and $H_2$ and convert them into $CH_4$. Normally, one does not want any flow processes or even any strong mixing of gas and aqueous medium in bioreactors, so as not to disturb the fermentation and thus possibly affect the yield negatively. But the inventor has discovered that methanogenic microorganisms should be brought strongly and permanently into contact with the gaseous mixture containing H2 and CO2, offering the gaseous mixture to the methanogenic microorganisms such that the contact surface between the methanogenic microorganisms and the gaseous mixture is increased as much as possible, so that the methanogenic microorganisms have the most optimal conditions to take up $CO_2$ and Hz. This is accomplished, for example, in that the gaseous mixture is mixed so much with the aqueous medium of the reactor, e.g., by means of a pump, preferably a driving jet pump, or by means of a compressor, that a formation of foam occurs.

Therefore, in a preferred embodiment the reaction boosting device of the device according to the invention is configured such that it disperses the gaseous mixture in the aqueous medium of the reactor of the device according to the invention. The dispersing is such that foam is formed when the gaseous mixture is introduced into the aqueous medium of the reactor of the device according to the invention.

The reactor of the device according to the invention is set up in one preferred embodiment as a tube reactor. Similar to tube photobioreactors, a tube reactor according to the invention is composed of one or more tubes. The tubes are constructed in horizontal or vertical orientation, e.g., alongside each other.

As already mentioned, the reaction boosting device is designed so that it increases the contact surface between the aqueous medium in which the methanogenic microorganisms are found and the gaseous mixture. This is accomplished by importing of energy, e.g., mechanical energy or pneumatic energy. The reaction boosting device can be configured so that it disperses the gaseous mixture in the aqueous medium of the reactor of the device according to the invention. The dispersal is such that foam is formed when the gaseous mixture is introduced into the aqueous medium of the reactor of the device according to the invention.

In another preferred embodiment of the device according to the invention the reaction boosting device has at least one trickling bed, one spray tower, one in-line mixer or one pump, preferably a driving jet pump or a compressor. In particular with the help of an in-line mixer, a pump, or a compressor, gaseous mixture is introduced into the aqueous medium so that the gaseous mixture is dispersed in the aqueous medium and ideally a foam is formed, which increases the contact surface so that the methanogenic microorganisms can take up $CO_2$ and $H_2$ effectively and/or in the largest possible amount. In the case of the present invention, an in-line mixer and/or a pump, preferably a driving jet pump, is more preferred.

"Methanogenic microorganisms" in the sense of the invention are those microorganisms which can use carbon dioxide ($CO_2$) and hydrogen ($H_2$) to make methane ($CH_4$), i.e., methane formers or methane-forming microorganisms. Therefore, methanogenic microorganisms can also be called methane-forming microorganisms. An example of such methanogenic microorganisms is methanogenic bacteria, so-called methane bacteria. Methane bacteria belong to the kingdom of the Arachaea and in this to the phylum Euryarchaeota. Methanogenic microorganisms belong to the classes Methanobacteriales, Methanococcales, Methanomicrobiales, Methanocellales, Methanosarcinales and Methanopyrales. In the context of the present invention, methanogenic microorganisms can but need not come from all of the aforementioned classes. It is therefore preferred that the methanogenic microorganisms are a mixture of different microorganisms of the phylum Euryarchaeota.

"Aqueous Medium" comprises aqueous liquids, preferably those in which methanogenic microorganisms can grow. The skilled person is familiar with such media. They may contain, e.g., vitamins, trace elements and/or heavy metals needed by such methanogenic microorganisms. Preferably the aqueous medium is not an ionic liquid. An ionic liquid consists of organics, whose ions hinder the formation of a stable crystal lattice due to charge delocalization and steric effects. Therefore, even low thermal energy is enough to overcome the lattice energy and break up the solid crystal structure. Thus, they are salts, which are liquid at temperatures below 100° C., without the salt being dissolved in a solvent such as water.

In a preferred embodiment, the device according to the invention moreover has a drainage mechanism, which is designed to drain away a gas from the at least one reactor. The gas can contain $H_2$, $CO_2$ and/or $CH_4$, preferably the gas contains $CH_4$. The quantitative fraction of CH4 in the gas can be at least 50%, 60%, 70%, 80% or more, such as 85% or 90% or more. The inventor has discovered that, by increasing the contact surface between the aqueous medium with the methanogenic microorganisms and the gaseous mixture, as explained more closely herein, the yield of methane can be greatly increased.

In another preferred embodiment, the device according to the invention also has a return mechanism, which is designed to return at least a portion of the gas to the feed mechanism. The return mechanism preferably has a pump or a compressor.

In another preferred embodiment, the device according to the invention also has a circulation mechanism, which is designed to circulate the aqueous medium through the at least one reactor. The circulation mechanism preferably has at least one pump, preferably a driving jet pump.

In another preferred embodiment of the device according to the invention, the feed mechanism has a device for enrichment of carbon dioxide from a gas mixture.

It is furthermore preferable for the feed mechanism of the device according to the invention to have a device for electrolytic splitting of water.

It is likewise preferred that the feed mechanism of the device according to the invention to be designed so that the gaseous mixture forms a turbulent flow when channeling $H_2$ and $CO_2$ into the at least one reactor.

Furthermore, it is preferred that the feed mechanism of the device according to the invention to be designed such that, in operation, the volume of introduced $H_2$ and $CO_2$ per hour exceeds the volume capacity of the at least one reactor by at least a factor of r 1, 2, 3, 4, 5, 10, 20, 25, 30, 50, 75, 100, 200, 300, 400, 500 or more.

Preferably, the pressure in the reactor of the device according to the invention is greater than or equal to 0.1; 0.2; 0.3; 0.4; 0.5; 0.6; 0.7; 0.8; 0.9; 1.0 bar or more.

Preferably, the methanogenic microorganisms are present in the form of macroscopic colonies (pellets) in the aqueous medium of the reactor of the device according to the invention. By pellets is meant macrocolonies, 1-5 mm in size, of methanogenic microorganisms, such as may occur in anaerobic upflow reactors (UASB, IC etc.) for anaerobic pretreatment of industrial wastewaters. Such pellets can be obtained from an anaerobic industrial wastewater treatment plant (such as a pulp plant or the food industry). Pellets are described, e.g., in Guiot et al. (2011). It is assumed that the anaerobic methanogenic microorganisms, presumably a mixed population of various methanogenic microorganisms, are found in the inside of a pellet, whereas aerobic microorganisms are more likely found on the surface and underlying layers. The aerobes, so to speak, protect the anaerobes against oxygen incursion. In the case of seeding of a device according to the invention, especially the reactor, after driving out the oxygen, for example by nitrogen or by means of a carbon source which is metabolized by the aerobes present, consuming oxygen, the methanogenic microorganisms begin to convert the supplied carbon dioxide and hydrogen into methane. Now, the inventor has discovered that such pellets are very advantageous for the aforementioned reasons, since when working with pellets and seeding the reactor of the device according to the invention no special precautions need be taken to create and maintain an anaerobic environment. Furthermore, the inventor has discovered that the pellets contain sufficient methanogenic microorganisms to begin the production of methane from carbon dioxide and hydrogen within a very short time in the reactor of the device according to the invention. Moreover, the inventor has found that a reactor of a device according to the invention, seeded with pellets, can again be easily started up and/or operated for production of methane even after a lengthy down time. For the mentioned reasons, pellets are a preferred source for methanogenic microorganisms which are used in the context of the present invention. Whether pellets used according to the invention contain methanogenic microorganisms can be easily tested by means of, e.g., the VITO Methanogenic Bacteria Test of Vermicon. Alternatively, pellets can be supplied with gas in a miniaturized device according to the invention, especially in a reactor with carbon dioxide and hydrogen, in a suitable aqueous medium and be tested for production of methane.

Therefore, the present invention in another aspect concerns the use of pellets, containing methanogenic microorganisms, for the seeding of a device according to the invention.

As already mentioned, the present invention concerns methods for production of methane in a reactor device by means of methanogenic microorganisms, which are present in the reactor device in an aqueous medium, by conversion of $H_2$ and $CO_2$ as reaction gas mixture, characterized in that during the conversion the contact surface between the aqueous medium with the methanogenic microorganisms and the gaseous mixture is increased by means of a reaction boosting device.

Preferably, in the method, the use or the device according to the invention, a mixture of methanogenic microorganisms of the phylum Euryarchaeota is used. The mixture is created, since one preferably uses pellets which contain the methanogenic microorganisms, not being otherwise characterized.

Preferably, the methanogenic microorganisms are supplied in the form of macroscopic colonies (pellets) to the aqueous medium.

For the methods, but also the devices and uses of the present invention, it can be advantageous for the molar ratio of $H_2$ and $CO_2$ in the gaseous mixture to be less than or equal to around 4:1. However, molar ratios greater than 4:1 can also be used. This may have the result that, due to the relative deficiency of $CO_2$, the pH value inside the reactor may rise. By adding appropriate substances, such as buffer systems or acids, however, the pH value can be set at the desired value.

The present invention also concerns the following aspects A1 through to A6:

A1. Method for biomethanization of $H_2$ and $CO_2$ by methanogenic bacteria, in a suitable environment for this (temperature, pH, redox, nutrients, etc.), in a submerse bioreactor, characterized in that
1.1. the conversion occurs at pressures greater than 0.1 or 1 bar,
1.2. the bacteria involved are supplied to the reactor in the form of macroscopic colonies, so-called pellets, such as can be produced in anaerobic upflow reactors (UASB, IC etc.), or are added in the form of pasty sludge from digestion towers, biogas plants, etc.,
1.3. $H_2$ and $CO_2$ are supplied to the reactor in a ratio less than or equal to roughly 4:1, but also greater than 4:1,
1.4. the reactor is mixed with a gas recirculation,
1.5. the conversion takes place in several reactor parts hooked up in series or several reactors in a cascade.

A2. Submerse bioreactor according to aspect A1, characterized in that it has
2.1. a liquid volume (1) and
2.2. a gas volume (2).

A3. Liquid volume (1) according to aspect 2.1., characterized in that this is divided into a
3.1. larger, gasified, upward flowing part (A) and
3.2. a smaller, nongasified, downward flowing part (B).
Alternatively, the liquid volume (1) according to aspect 2.1 is characterized in that it is divided
3.1 one or more gasified part(s) (A) or
3.2 into one or more gasified part(s) (A) and one or more nongasified part(s) (B).

A4. The internal gas recirculation according to aspect 1.4. characterized in that
4.1. gas from the gas-carrying volume part (2) according to aspect 2.2. is introduced into the upflowing part (A) according to aspect 3.1. with suitable means,
4.2. the gas quantity recirculated per unit of time is greater than the gas quantity supplied to the reactor in the same period of time.
Alternatively, the internal gas recirculation according to aspect 1.4., characterized in that
4.1 gas from the gas-carrying volume part (2) according to aspect 2.2. is introduced into the gasified part(s) (A) according to aspect 3 by suitable means.

A5. The cascade according to aspect 1.5., characterized in that
5.1. the gas recirculation according to aspect 1.4. occurs separately for each reactor or reactor part or jointly for several such units,
5.2. these or subgroups of these are located together in a water space (C) and are jointly tempered by this.

A6. The submerse bioreactor according to aspect 1, characterized in that this has suitable devices for defoaming, such as defoamer dosage (6), foam breaker (7) or foam traps (7).

For the reference symbols, refer to the reference symbols used in FIGS. 7 to 10, which are given below the legend to FIG. 10.

BRIEF DESCRIPTION OF THE FIGURES

Nonlimiting Examples and Figures

With the aid of the enclosed representations (figures) and sample embodiments, the invention shall be explained more closely.

FIG. 3: Flow chart of a sample device for production of methane by means of methanogenic microorganisms making use of a submerse reactor FIG. 4: Flow chart of a sample device for production of methane by means of methanogenic microorganisms making use of a spray tower

DETAILED DESCRIPTION OF SPECIFIC SAMPLE EMBODIMENTS OF THE INVENTION

Figure 1:
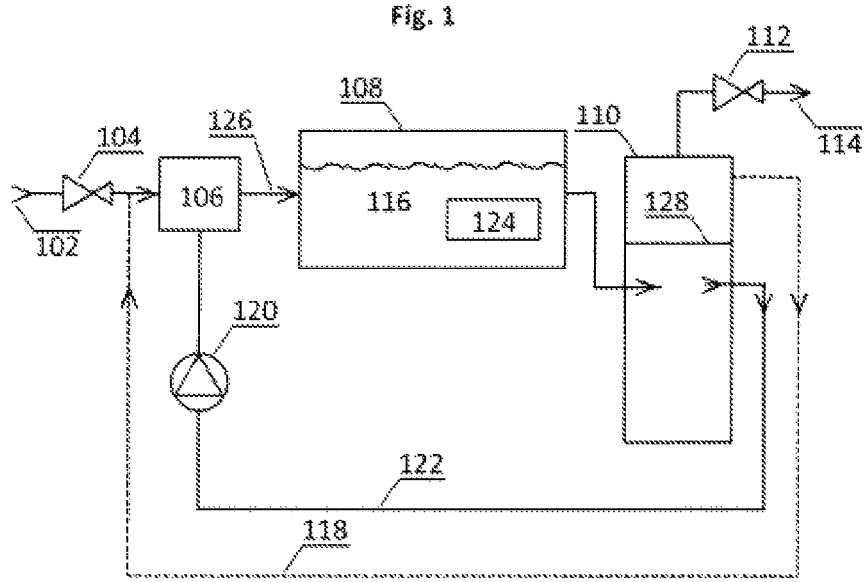
FIG. 1: Flow chart of a sample device for production of methane by means of methanogenic microorganisms making use of a tube reactor

FIG. 1 shows a sample embodiment of a device 100 for production of methane by means of methanogenic microorganisms by conversion of hydrogen and carbon dioxide. The sample device 100 has a reactor 108. An inlet line 102 is connected across a first valve 104, such as a first pressure sustaining valve 104, to a first inlet of a nozzle 106, for example, a driving jet nozzle. The nozzle 106 is connected across a corresponding line to the reactor 108. The reactor 108 is connected at its end by means of a line to an inlet of a gas separation device 110. The gas separation device 110 can be filled with a liquid, such as water, and it has three outlets. At a first outlet 114, a gaseous phase can be taken away across a second valve 112, such as a second pressure sustaining valve, containing at least the end product of the microbial conversion, the methane gas, or consisting essentially of this. By a second outlet, optionally a portion of the same gaseous phase can be drained from the gas separation device and supplied via a first return branch 118 to the nozzle 106. The gaseous phase can be fed by means of a separate line to the nozzle 106 or it can be fed into the line by means of which the first valve 104 is connected to the nozzle 106. The first return branch 118 is an optional device, especially in the case of sufficiently long tube reactors, which is not essential to the function of the invention presented here, but which can be entirely suitable for the optimization of its operation. At a third outlet of the gas separation device 110 a liquid phase can be drained away and supplied by means of a second return branch 122, in which a pump 120 is provided, to the nozzle 106.

In the sample embodiment represented in FIG. 1, the reactor 108 is a tube reactor. By a tube reactor is meant here a tubular container in which the methanogenic microorganisms are contained, and in which a microbial conversion reaction takes place, during which methane is made from $H_2$ and $CO_2$. The $H_2$ and $CO_2$ together form the substrate gas—the starting product of the microbial conversion reaction. These two gases can be supplied separated from each other by means of separate lines or already as a gas mixture by means of one line to the nozzle 106. The latter case is implemented in the embodiment shown in FIG. 1. The reactor 108 can be designed so that its interior can be maintained at a particular temperature which ensures an optimal course of the reaction. In the present case of production of methane by means of methanogenic microorganisms, the temperature can be for example in a range of around 30° C. to around 80° C., for example in a range of around 40° C. to around 70° C., for example at around 40 to around 50° C. In the reactor 108 there is present an aqueous medium 116, and the methanogenic microorganisms are present in the aqueous medium 116. The aqueous medium 116 can be a gas/liquid mixture, for example a foamy gas/water mixture. The substrate gas, which contains $H_2$ and $CO_2$, is fed by means of the nozzle 106 via a feed mechanism 126 to the reactor 108. The feed mechanism 126 can be a correspondingly designed pipe system, which is arranged to introduce a fluid into the reactor 108. In the context of this description, a fluid can mean a gas, a liquid, or a mixture thereof, such as a finely atomized liquid, which is furthermore mixed with a gas. Of course, other substances such as additives encouraging the microbial conversion reaction, such as heavy metals in small amounts which are partly required by methanogenic microorganisms, can also be conveyed into the reactor 108.

By means of the first return branch 118 the gaseous phase from the gas separation device 110 can be fed to the nozzle 106 and thus recycled. The gaseous phase taken away by means of the first return branch 118 can involve predominantly components of the substrate gas which have not been converted to methane in the reactor 108. These unreacted "residues" can be so to speak recycled in this way and are again available to the microbial reaction. The first return branch 118 can be omitted in very long tube reactors 108, since the substrate gas introduced at the inlet of such a tube reactor 108 is converted with high probability by the end of the reactor 108. In other words, it can be assumed that with increasing length of the tube reactor 108 the portion of the unreacted substrate gas at the end of such a reactor becomes increasingly smaller.

The nozzle 106 arranged between the first valve 104 and the reactor 108 serves to introduce at least the substrate gas into the reactor 108 such that at the same time a recirculation or throughput of the liquid medium 116 with the substrate gas so introduced takes place. By means of the nozzle 106 the kinetic energy of the substrate gas can be increased before it is introduced into the reactor 108. In this way, the substrate gas introduced can be as it were blown into the aqueous medium containing the methanogenic microorganisms, producing a strong recirculation of the aqueous medium 116. In other words, by introducing the substrate gas into the reactor 108 by means of the nozzle 106 one can produce numerous gas bubbles which push the aqueous phase 116 through (hereinafter called the dynamic case). In this way, the reaction surface between the substrate gas and the aqueous medium 116 is drastically increased as compared to the case (hereinafter called the static case) when the substrate gas is introduced into a tube reactor 108 without the above-described recirculation of the aqueous phase 116.

The driving jet can be formed by the nozzle 106 with the help of the liquid phase which is drained off from the gas separation device 110. The nozzle 106 can be, for example, a jet pump in which, depending on the design of the device, the gaseous medium or the liquid phase drained away from the gas separation device 110 can be used. The liquid phase drained away through the second return branch 122 is the aqueous medium 116 from the reactor 108. The gas separation device 110 can be seen functionally as a settling or separation device. In the reactor 108, due to the turbulent mixing processes, the aqueous medium 116 can be present as a foamy gas/water mixture. In other words, the liquid containing the methanogenic microorganisms is heavily enriched with the gaseous phase—methane and residues of the substrate gas. In this state, the aqueous medium 116 is transferred to the gas separation device 110 and a separation of the gaseous phase from the liquid phase occurs there, while the aqueous medium 116 can still be foamy. This gas separation process can naturally occur by uplifting of the gaseous phase (unreacted residues of the substrate gas and methane) from the mixture 116 of liquid and gas. The liquid essentially cleansed of the gaseous phase together with the methanogenic microorganisms can then, as shown in FIG. 1, be removed at the third outlet of the gas separation device 110 and be fed by means of the pump 120 across the second return branch 122 to the nozzle 106 and used to form the driving jet entering the reactor 108. In this way, a closed circulation of the aqueous medium 116 can be achieved.

The gas which can be drained away at the second outlet of the gas separation device 110 and which can be fed to the nozzle 106 by means of the optional first return branch 118 contains essentially only methane in the optimal case, and possibly slight residues of the unreacted substrate gas. The recirculation rate of the gaseous phase from the gas separation device 110 can be adapted to the length of the reactor 108 and, as already mentioned, will tend toward zero in sufficiently long reactors 108, in which the recirculated gaseous phase from the gas separation device 110 consists essentially of methane. Since the production method presented here is very efficient, i.e., thanks to the strong mixing of the aqueous medium 116 in the reactor 108 with the substrate gas, conversion rates of more than 90% for example, more than 95% for example, practically 100% for example can be achieved. When the first recirculation branch 118 is present, the recirculation rate of the gaseous phase from the gas separation device 110 can always be larger than the feed rate of the substrate gas into the reactor 108 by means of the inlet line 102, for example by factors on the order of 1 to 100, for example, to 200 for example, to 500 for example, to 1000 or more, for example. With very long tube reactors 108, as mentioned above, almost the entire substrate gas is converted to methane. An appropriately designed return branch 118 can also be provided in this case, despite a vanishingly small fraction of the substrate gas residue in the recirculated gas. Regardless of the conversion rate inside the reactor 108, with the help of a high gas recirculation rate by means of the first return branch 118, which thus corresponds functionally to a recirculation branch, the gas fraction in the gas/water mixture inside the reactor 108 and thus the degree of turbulence can be increased. By means of the gas recirculation, the mixing of the gas/water mixture inside the reactor 108, i.e., the contact time and contact surface between these two phases, can thus be increased.

The gas mixture located above the liquid surface 128 in the gas separation device 110 during the operation of the device 100 contains the product gas and, depending on the efficiency of the conversion, small to vanishingly slight residues of unreacted substrate gas. This gas mixture can be drained off entirely or partially at the first outlet 114 from the device 100 and optionally recirculated by means of the first return branch 118 to the reactor 108. In other words, a gaseous phase of identical composition is drained off at the first outlet 112 and at the second outlet (belonging to the optional first return branch 118).

Equilibrium generally obtains for a particular $H_2/CO_2$ ratio in the reactor 108 or in the gas separation device 110: a $CO_2$ concentration in the gas corresponds to a $CO_2$ concentration in the aqueous medium 116. If the entire $CO_2$ is converted, the pH value in the aqueous medium 116 will rise, which may be undesirable. Therefore, the feeding of the substrate gas at the inlet line 102 can be adjusted so that both in the gas phase drained off at the first outlet 114 and thus also at the second outlet a residue of $CO_2$ always remains, for example around 1% to around 2%. A total conversion of $H_2$ on the other hand does not result in shifting of the pH value. In order to stabilize the pH value it can thus be beneficial to supply the substrate gas to the device 100 by means of the inlet line 102 in a ratio of around 4:1 ($H_2$ to $CO_2$) or less.

The introducing of the substrate gas into the reactor 108 by means of the nozzle 106, resulting in the mixing of the aqueous medium 116 with the substrate gas, ensures that a much larger number of the methanogenic organisms per unit of time come into contact with the substrate gas in the dynamic case and therefore a larger number of the methanogenic organisms can produce methane per unit of time than in the static case. Approximately speaking, the reaction or contact surface between an aqueous medium 116 present in the reactor and the substrate gas corresponds in the static case to the surface of the medium. In the dynamic case, however, or according to the teaching of the invention as explained in this specification, this surface is much larger, since there must be added to the already roughened and thus larger surface of the aqueous medium 116 in the reactor 108 (indicated by the wavy line inside the reactor 108) the sum of the surfaces of the gas bubbles permeating the aqueous medium 116, wherein the gas bubbles at the beginning of the tube reactor 108 tend to have only substrate gas, and at its end the gas bubbles ideally can have only the end product methane and in between the gas forming the bubbles can have any given mix ratio of substrate gas and methane.

Moreover, for further increasing of the contact surface between the substrate gas and the aqueous medium 116 the reactor 108 can optionally have at least one mixing element 124. The at least one mixing element 124 can be at least one element which is suitable to mix the substrate gas present in the reactor 108 with the aqueous medium 116. The at least one mixing element 124 can be, for example, a mechanically dynamic element and be designed for example as a rotating water wheel, a jet stream mixer, a turbine stirrer, a propeller stirrer, or perhaps an in-line mixer, this being by no means considered to be an exhaustive listing of possible mixing elements. But the at least one mixing element 124 can also be a mechanically static element, such as an atomization screen, which converts larger substrate gas bubbles into smaller substrate gas bubbles. The at least one mixing element 124 can also have at least one of both a mechanically dynamic and a mechanically static element.

As shown moreover in FIG. 1, the sample device 100 for the production of methane by means of methanogenic microorganisms has at least two valves, namely, the first valve 104 and the second valve 112. Clearly, as needed, additional fluidic elements can be provided in the device 100, such as further valves, flow meters and compressors. By means of the first valve 104 and the second valve 112 the part of the sample device 100 between the inlet line 102 supplying the substrate gas and the first outlet 114 of the gas separation device 110 draining off the gaseous phase containing the methane gas can be exposed to a pressure gradient, which makes possible the charging of the reactor 108 and creates a fluid flow from the reactor 108 to the gas separation device 110. The lower pressure level (i.e., the pressure at the second valve 112) of the pressure gradient can be at ambient pressure (atmospheric pressure). But if need be, the lower pressure level can also be at a pressure higher than ambient pressure, for example, around 50 mbar, for example 100 mbar, for example 200 mbar, for example 500 mbar or more above ambient pressure. This may prove to be beneficial, as one can thus effectively prevent oxygen from getting into the device 100, which usually can have negative impact on the lifetime and/or number of the methanogenic microorganisms. The first valve 104 furthermore can also be used to control the quantity of substrate gas supplied to the reactor 108 per unit of time and its mix ratio. The latter can also be adjusted by providing separate feeds for $H_2$ and $CO_2$ and two corresponding first valves.

The effective conversion of the substrate gas by means of the methanogenic microorganisms into the product gas methane is based on a highly turbulent gas/water/bacteria mixing inside the tube reactor 108 with an adequate flow rate of the aqueous medium 116, which when using static in-line mixers can be for example in the range of around 3 m/s to around 10 m/s, for example in the range of around 3 m/s to around 5 m/s. When using dynamic in-line mixers with independent motor drive unit, no flow rate is dictated.

The boosted reaction rate inside the reactor 108 can be accomplished by a highly turbulent mixing of the aqueous medium 116 with the substrate gas. Preferably, the gas volume introduced into the reactor 108 per hour is greater than the volume capacity of the tube reactor 108 itself. The ratio of the gas volume introduced into the reactor 108 per hour to its volume capacity can be for example around 5:1 or more, for example around 10:1, for example around 25:1, for example 50:1 or more. These values pertain to the gas feed at the feed mechanism 102.

Based on these figures, a little mathematical estimate shall be made to demonstrate the possible capability of the concept presented here. If one starts from a ratio of the gas volume introduced into the reactor 108 per hour to its volume capacity of 5:1, for each cubic meter of reactor volume with an almost complete conversion of the substrate gas according to the teaching of this specification 1 $m^3$ of methane can be formed per hour. 1 $m^3$ of methane has an energy content of around 10 kWh. It follows from the development of 1 $m^3$ methane per hour per 1 $m^3$ of reactor volume, at complete conversion of the substrate gases to methane, that a corresponding reactor will have a power of around 10 kW per cubic meter. Thus, a reactor 100 $m^3$ in size would have a power of 1 MW. If one increases the gas throughput ratio to 25:1 per hour, with complete conversion of the substrate gases to methane one can realize a reactor plant with 1 MW power with only 20 $m^3$ of reactor volume. However, it must be stressed that this is a sample calculation, which is meant to illustrate quantitatively a possible operating scenario of the device for production of methane by means of methanogenic microorganisms as an estimation and should in no way be taken as limiting the power spectrum of the concept presented here.

The highly turbulent mixing of the aqueous medium 116 with the substrate gas inside the reactor 116—by whatever means this is brought about—ensures a distinct increasing of the contact surface between the aqueous medium 116 with the methanogenic microorganisms and the substrate gas, which in turn ensures a distinctly higher reaction rate inside the reactor 108 as compared to the static case mentioned above. In view of the intense mixing of the aqueous medium 116, one can speak in the present case of a rather atypical operation of the tube reactor 108 of the sample device 100 for the production of methane by means of methanogenic microorganisms, since tube reactors of this kind used in chemistry usually have a negligible axial mixing in operation. But in the case presented here of the production method for methane by means of the 100 from FIG. 1 as a sample embodiment it is this mixing which ensures a boosted reaction rate inside the reactor and thus a distinctly increased methane yield as compared to customary production conditions. In this context, the nozzle 106 in FIG. 1 can be seen in terms of its function as a reaction boosting device, since the driving jet produced by it brings about a recirculation of the aqueous medium 116 in the reactor 108 and thus the increased reaction rate can be achieved by said increasing of the contact surface. The mixing element 124 optionally provided in the reactor 108 also contributes to the recirculation of the aqueous medium 116 inside the tube reactor 108 and should thus also be assigned functionally to the reaction boosting device.

The sample embodiment of the device 100 for production of methane described thus far and represented in FIG. 1 embodies one possibility of obtaining a highly efficient conversion of the substrate gas into methane, according to the teaching presented here. In the following, on the basis of the device from FIG. 1, further sample embodiments shall be described. Starting from FIG. 1, functionally identical elements shall be given the same reference number and will not be described again in greater detail.

Figure 2:
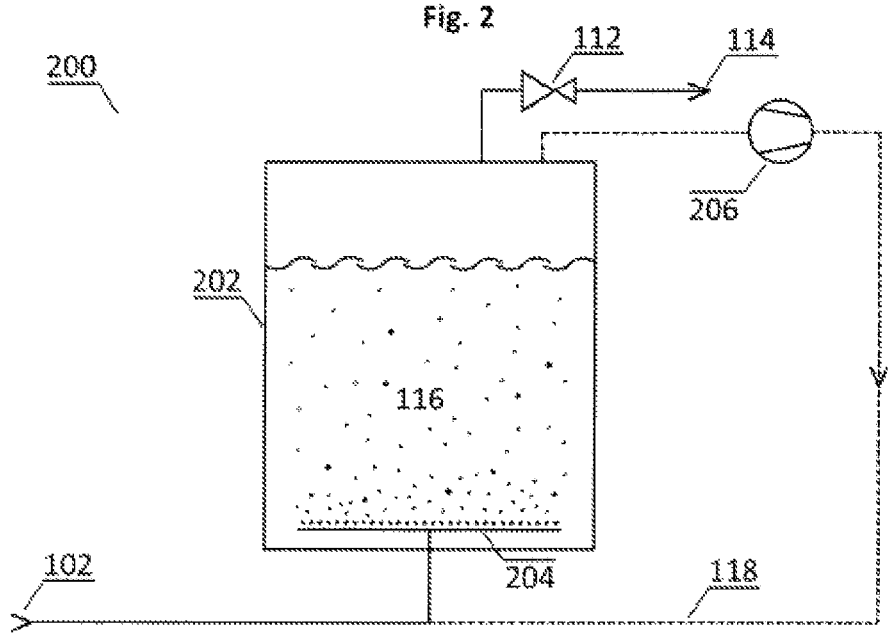
FIG. 2: Flow chart of a sample device for production of methane by means of methanogenic microorganisms making use of a stirred tank

Another sample embodiment of a device 200 for the production of methane by means of methanogenic microorganisms is represented in FIG. 2. The device 200, in contrast with the embodiment represented in FIG. 1, is based on a stirred tank 202 (STR, stirred tank reactor or CSTR, continuous stirred tank reactor), in which the aqueous medium 116 is present, the stirred tank 202 being classified in the category of the submerse reactors. The stirred tank 202 has a stirrer 204, which acts functionally as a mixing element. In the stirrer 204, for example on the surface of its rotor blades, openings can be provided, from which gas can emerge. As in the device 100 shown in FIG. 1, here as well the substrate gas is supplied by means of the inlet line 102 to the reactor. The substrate gas can then emerge, as shown in FIG. 2, from the stirrer 204 itself, for example from its rotor blades during its rotation (stirring motion) or alternatively be introduced into the aqueous medium 116 by means of a separate channeling device independent of the stirrer 204. Such a channeling device can be arranged for example on the bottom of the stirred tank 202 and can introduce the substrate gas into the aqueous medium 116 through a plurality of openings. In either case, an optimal mixing of the substrate gas with the aqueous medium 116 is achieved. Thanks to the rotation of the stirrer 204 or the interaction of the stirrer 204 with the channeling device arranged below it (not shown in FIG. 2), an optimal mixing of the substrate gas with the aqueous medium 116 can be achieved, as illustrated by the gas bubbles rising in the aqueous medium 116, shown in FIG. 2. A strong formation of gas bubbles may be desirable, since this can significantly increase the reaction surface between the substrate gas introduced into the stirred tank 202 and the aqueous medium 116. From this standpoint, the formation of many small gas bubbles may be better than the formation of a few larger gas bubbles. Moreover, a large gas recirculation may be beneficial, which can bring about an increased contact time and contact surface between the aqueous medium and the substrate gas. The methanogenic microorganisms in the aqueous medium 116—in addition to the supplying at the interface boundary between aqueous medium 116 and the gas phase above it inside the stirred tank 202—can be supplied through the surface of each gas bubble with the product gases $H_2$ and $CO_2$, so that in a first approximation the entire volume of the liquid medium 116 can be utilized for the formation of methane. In order to promote the formation of small gas bubbles, the stirrer 204 can have corresponding elements, such as screens or other fine-mesh structures on its surface.

By means of the first return branch 118 the gaseous phase, possibly containing unreacted substrate gas which collects above the surface of the aqueous medium 116 inside the stirred tank 202, can be taken away and mixed in with the substrate gas supplied at the inlet line 102 by means of a compressor 206 and thus ensure a boosted turbulent mixing of the phases inside the stirred tank 202.

A further sample embodiment of a device 300 for the production of methane by means of methanogenic microorganisms is shown in FIG. 3. The device 300 is based on a submerse reactor 302. On the floor of the submerse reactors 302 is arranged the nozzle 106, for example a driving jet nozzle, by means of which a driving jet is created and can be directed from the floor of the submerse reactor 302 into the aqueous medium 116. With the nozzle 106, one can accomplish on the one hand a forced convection of the aqueous medium 116 under energy input, and on the other hand the aqueous medium 116 can be turbulently mixed with the substrate gas. In functional terms, the nozzle 106 thus corresponds to the reaction boosting device, while of course at least one mixing element 124 can be additionally provided in the submerse reactor 302, which has been described further above in conjunction with the device shown in FIG. 1. The nozzle 106 is provided with fluids in the same way as already described in conjunction with the device 100 shown in FIG. 1, namely, with the substrate gas, with the aqueous medium 116 via the second return branch 122 and optionally with the gaseous phase from the inside of the submerse reactor 302.

Yet another sample embodiment of a device 400 for the production of methane by means of methanogenic microorganisms is shown in FIG. 4, in which a spray tower 402 is used as the reactor. The substrate gas is introduced by means of the first valve 104 into the interior of the spray tower 402. By means of the second return branch 122 the aqueous medium 116 is transported upward to a dispersion device 404, such as an atomization nozzle. In this sample embodiment, the aqueous medium 116 is atomized into tiny droplets 406 and sprayed into the spray tower 402 at its ceiling. Thus, in functional terms, the dispersion device 404 is a reaction boosting device. The tinier the droplets 406 produced by the dispersion device 404, the greater the contact surface between the aqueous medium 116 and the substrate gas and the greater the reaction rate of the conversion. The introducing of the substrate gas via the inlet line 102 can also occur, in departure from the representation in FIG. 4, beneath the surface of the aqueous medium 116 in the spray tower 402, for example, via an outlet opening or a corresponding arrangement of closely spaced outlet openings, so that the substrate gas can at first pass through the aqueous medium 116 present in the spray tower 402 as a liquid column and a methane gas production can also occur already in this liquid column. Generally speaking, the reaction boosting devices presented in this application can be combined with each other in any expedient manner in order to maximize the contact surface between the substrate gas and the aqueous medium 116 and thus the methanogenic microorganisms in order to maximize the reaction rate of the methane production.

Figure 5:
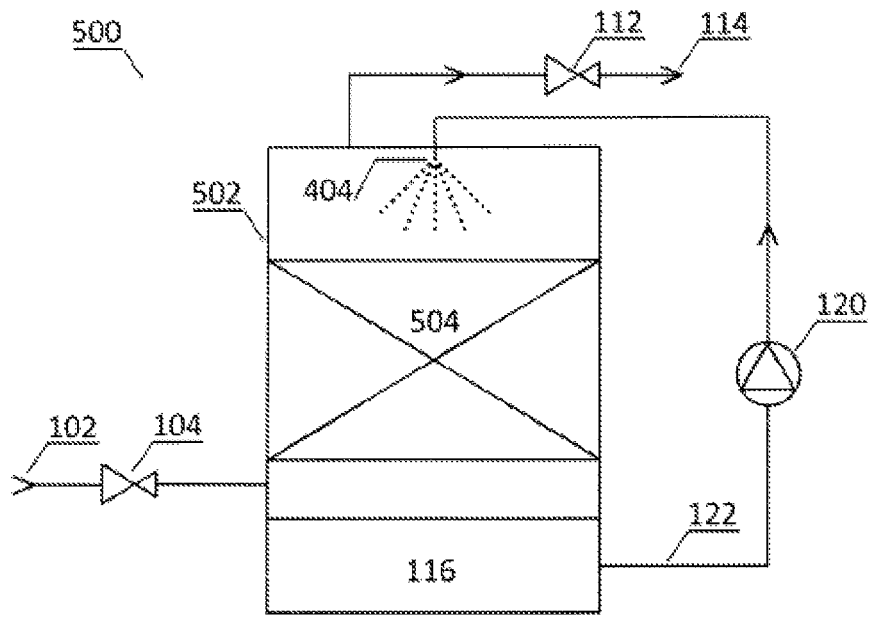
FIG. 5: Flow chart of a sample device for production of methane by means of methanogenic microorganisms making use of a trickle-bed reactor

FIG. 5 shows another embodiment of the device for the production of methane by means of methanogenic microorganisms, in which a trickling-bed reactor 502 is used. The device 500 resembles the layout of the device shown in FIG. 4. In addition, however, there is provided inside it a porous or honeycomb matrix 504, on which the liquid medium 116 sprayed in from above can trickle down. The interior surface of the matrix 504, for example the size of the pores or honeycombs inside it, defines the reaction surface here. The matrix 504 can be coated with or consist of a material such as glass, plastic, lava ash which ensures a uniform and continuous wetting of the matrix 504 and/or prevents too fast a seepage of the aqueous medium 116 through the matrix 504. In the device 500 shown in FIG. 5 for the production of methane, the reaction boosting device is formed from the matrix 504 and the dispersion device 404, since the interplay of these two devices enables a much increased reaction surface between the aqueous medium 116 and the substrate gas as compared to the static case.

Figure 6:
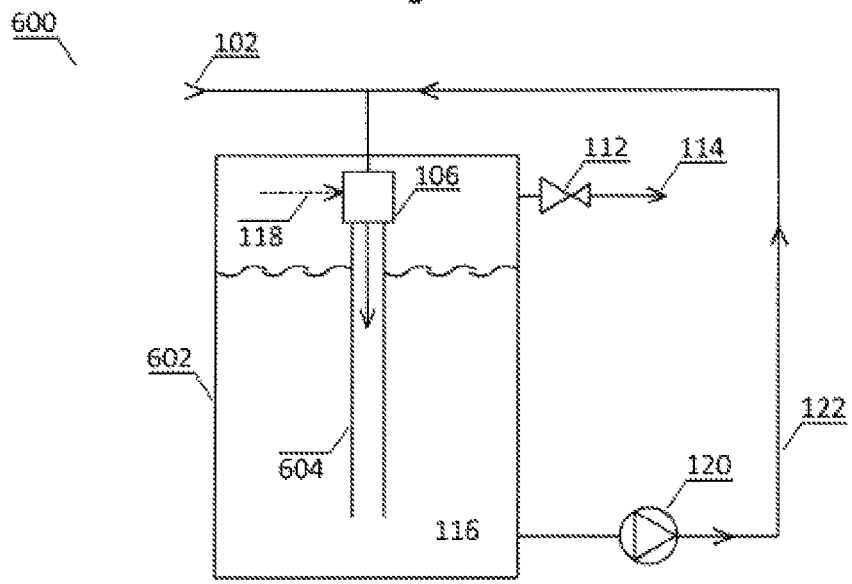
FIG. 6: Flow chart of a sample device for production of methane by means of methanogenic microorganisms making use of a jet reactor

Yet another embodiment of the device for the production of methane by means of methanogenic microorganisms is shown in FIG. 6, in which a driving jet reactor 602 is used. The substrate gas and the aqueous medium 116 are supplied from the outside to the nozzle 106, such as a driving jet nozzle, arranged on the ceiling or in the upper section of the jet reactor 602. The nozzle 106 moreover can directly aspirate the gaseous phase from the inside of the jet reactor 602, which corresponds to the optional first return branch 118. The driving jet produced by the nozzle 106 can be introduced into or be directed into the aqueous medium 116, resulting in its turbulent mixing with the substrate gas. For example, the driving jet can be introduced by means of a pipe 604 into the aqueous medium 116, while fine openings can be provided on the sides of the pipe 604, through which already a portion of the substrate gas flowing downward can be introduced into the aqueous medium 116. It may be beneficial for the end of the elongated pipe 604 to be situated near the bottom of the jet reactor 602, so that the driving jet passes through a relatively large portion of the aqueous medium 116.

Figure 7:
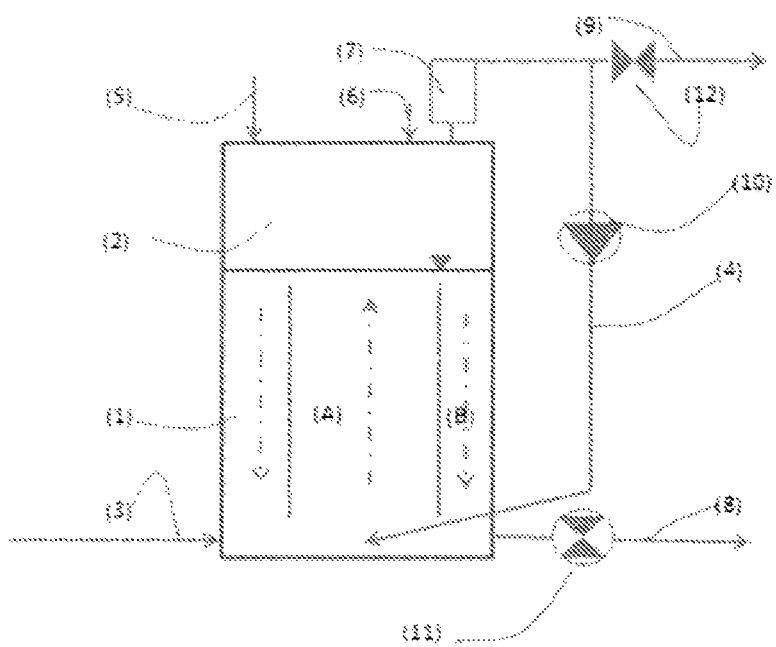
FIG. 7: Flow chart of a submerse reactor for conversion of gaseous substrates. For example, methane bacteria are introduced as compact pellet in a submerse bioreactor and gasified with $H_2$ and $CO_2$ at pressure under physiological conditions. An effective phase transition of the gaseous substrate is achieved by an internal recirculation (4) of gases from the reactor gas space (2) into the liquid phase (1). Several reactors (Rn) or reactor parts with different conditions are operated as a cascade in series. Advantages of the method: low temperatures, high organism density, short startup times, flexible operation, simple controls.

FIG. 7 shows a sample embodiment of a device for the production of methane (formula symbol $CH_4$) by means of methanogenic microorganisms by conversion of hydrogen (formula symbol $H_2$) and carbon dioxide (formula symbol $CO_2$). This device is a submerse reactor. According to the invention, methanogenic macrocolonies, so-called pellets, are added in high densities to a submerse bioreactor predominantly filled with nutrient liquid. The supplying of the organisms with their substrate, a hydrogen/carbon dioxide mixture, is done by an intensive gasification of the nutrient liquid in which the organisms are present. This is accomplished in that the reactor is operated under greater than atmospheric pressure (12), in order to increase the solubility of the hydrogen. Furthermore, the reactor is mixed by an internal gas recirculation (4). The reactor has a gasified upstream part (A) and nongasified downstream part (B). The gas from the gas phase lying on top of the liquid phase is introduced under pressure into the gasified part and thus produces an upward flow of a gas/liquid/pellet mixture. In the upper part of the reactor, the gas is given off to the gas phase, so that a pellet/nutrient medium mixture can flow back down in the nongasified part (B). The recirculated gas quantity (4) here per unit of time is much greater than the quantity of the gas mixture (3) supplied to the reactor.

Figure 8:
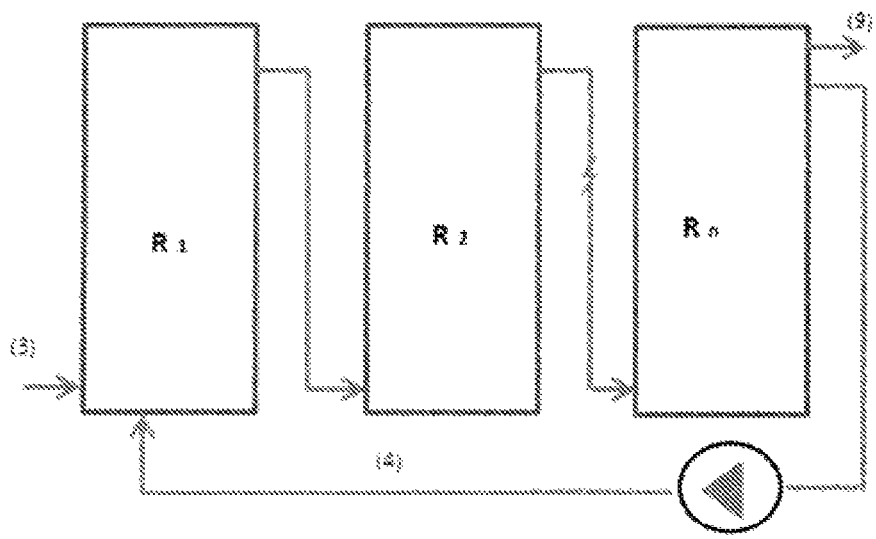
FIG. 8: Flow chart of a cascade of reactors $R_1$ to $R_n$ with common gas recirculation
Figure 9:
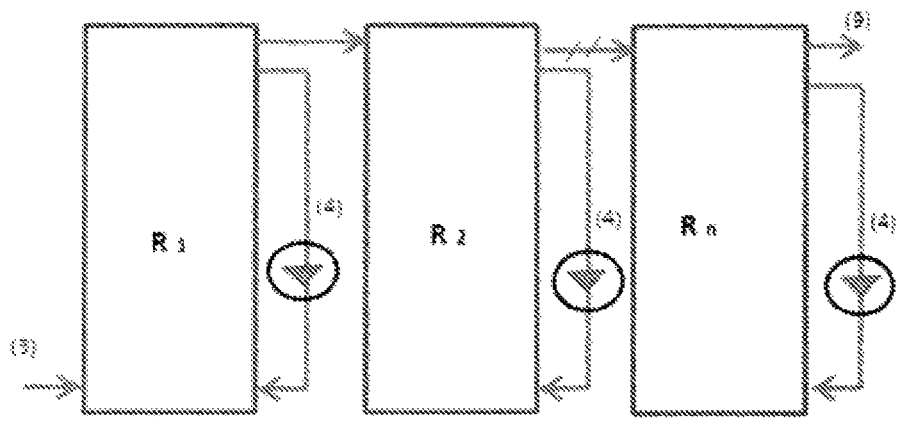
FIG. 9: Flow chart of a cascade of reactors $R_1$ to $R_n$ with separate gas recirculation
Figure 10:
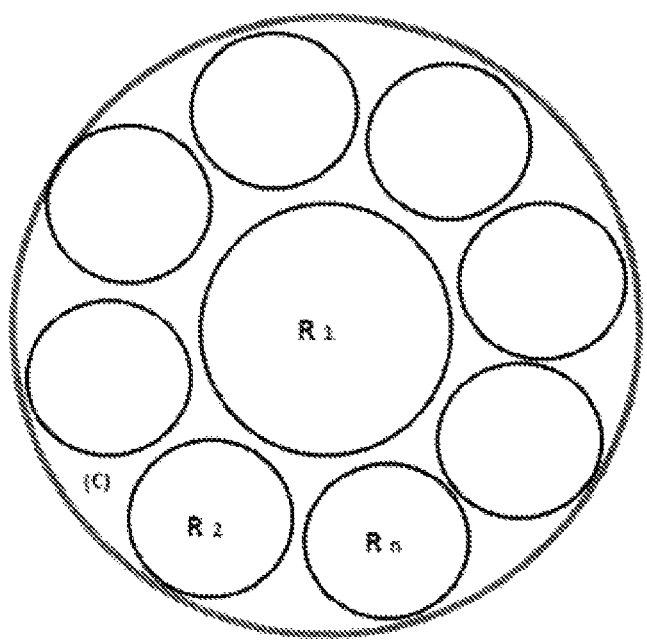
FIG. 10: Arrangement of several reactors ($R_1$ to $R_n$) in a common water body (C), cross section List of References for FIGS. 1 to 6
100 Device for production of methane with a tube reactor
102 Inlet line
104 First valve
106 Nozzle
108 Reactor (designed as a tube reactor)
110 Gas separation device
112 Second valve
114 First outlet
116 Aqueous medium
118 First return branch
120 Pump
122 Second return branch
124 Mixing element
126 Feed mechanism
128 Liquid surface
200 Device for production of methane with a stirred tank
202 Reactor (designed as a stirred tank)
204 Stirrer
300 Device for production of methane with a submerse reactor
302 Reactor (designed as a submerse reactor)
400 Device for production of methane with a spray tower
402 Reactor (designed as a spray tower)
404 Dispersion device
500 Device for production of methane with a trickle-bed reactor
502 Reactor (designed as a trickle-bed reactor)
504 Matrix
600 Device for production of methane with a trickle-bed reactor
602 Reactor (designed as a driving jet reactor)
List of References for FIGS. 7 to 10
(A) Gasified reactor part with up flow
(B) Nongasified reactor part with down flow
(C) Water body by which several reactors can be tempered
(1) Primarily water filled volume fraction of the reactor
(2) Primarily gas filled volume fraction of the reactor
(3) Gas supply
(4) Gas recirculation
(5) Inlet for nutrient and bacteria supply, pH adjustment, taking samples, etc.
(6) Defoamer dosage
(7) Defoaming device, foam trap
(8) Drainage of solid, liquid and dissolved products from (1)
(9) Drainage of gaseous products from (2)
(10) Gas recirculation pump
(11) Shutoff element
(12) Pressure sustaining valve

Several such submerse reactors ($R_1$ to $R_n$) can be operated in series as a cascade one after another (see FIGS. 8, 9 and 10). A particular gas quantity flows from the front reactor to the one behind it. If the reactors are operated with different gas pressures, different conditions and a plug flow will be established in the reactors. In this way, the gaseous substrate can be extensively converted to methane. This method can make a contribution to utilizing unusable peak production of electricity in order to convert it into a storable form: energy-rich methane. The method consumes carbon dioxide, which need not be provided in pure form. As compared to chemical methods, the method of biomethanization according to the invention takes place under natural conditions. Methane bacteria can survive without nutrition for lengthy periods of time. Thus, they can respond in flexible manner to the demand.

In all the embodiments presented here of the device for production of methane by means of methanogenic microorganisms the $CO_2$ can be obtained from a smoke gas, such as a trash incinerator or a power plant, such as a coal-fired power plant. For this, the device according to the invention can have a concentration device, having for example a pressurized tank filled with water, through which smoke gas is taken. Since $CO_2$ has better solubility as compared to $N_2$ and $O_2$, the water can become enriched with $CO_2$ under pressure. Then, by reducing the pressure, the smoke gas can at first be removed from the concentration device. By a further pressure reduction the $CO_2$ can then be released from the water and supplied as substrate gas to the nozzle 106 and used, for example, together with the recirculated aqueous medium 116 to form the driving jet. Oxygen residues can be removed chemically or biologically before feeding to the nozzle 106.

As compared to chemical methods using catalysis, the method according to the invention can also be carried out with gases that are not pure. Steps to purify the gases are done away with. As compared to other methods of biomethanization, defined biomass densities can be established here and reproduced as needed. Furthermore, a good gas supply of the organisms is assured by the internal recirculation of the gas.

Sample Embodiment 1

Load water in reactor with nutrient salts for freshwater medium per Widdel (1980) as well as permillage trace elements per Immhoff-Stuckle et al. (1983). Heat water in the reactor to around 60-70° C., drive out the atmosphere with $N_2$. Close reactor. Let water cool down under $N_2$ atmosphere to around 40° C. and add $N_2$ up to a pressure of around 0.2 bar. Add a permillage vitamin solution per Balch et al. (1979). Reduce with NaS to <−0.2 V. Add active methanogenic bacterial macrocolonies, so-called pellets, from an anaerobic industrial wastewater treatment plant (such as a pulp plant or the food industry) in sufficient concentration (around 1% dry substance). Adjust temperature from 35 to 38° C. and pH to around 7. Start mixing of the reactor. Charge reactor with a defined quantity of substrate gases ($Hz/CO_2$) per unit of time in a ratio of around 4:1 with a pressure of 0.2 bar. Maintain a pressure in the reactor of 0.2-0.1 bar. Release the resulting gas mixture from the reactor at a pressure of >0.2-0.1 bar.

Literature

Balch, W. E.; Fox, G. E. Magrum, L. J.; Woese, C. R.; Wolfe, R. S. (1979): Methanogenisis: Reevaluation of a unique biological group. Microbial. Review 43, 260-296

Bajohr et al.: Storage of regeneratively produced electrical energy in the natural gas infrastructure, DVGW study, 2011

Brunner, M. (1987): "Anaerobic microbial decomposition of 3-chlorobenzoic acid to biogas" (1987), Inaugural Dissertation for the title of doctor at the School of Mathematical and Natural Sciences of the University of Dusseldorf Brunner, M.; Schoberth, S. M.; Sahm, H. (1987): "Anaerobic microbial decomposition of halogenated aromatics to biogas", *Chem.-Ing.-Tech.* 59 (1), 55-57

Brunner, M. (1989): "New experiences with anaerobic wastewater purification by means of UASB reactors in the paper industry", *Allgemeine Papierrundschau* November 1989

Brunner, M., Dietrich, P. (1988): "Concepts for anaerobic wastewater purification in the fruit juice industry", *Confructra* 32 III/IV, 118-125

"The natural gas grid as a system integrator for more constant wind and solar energy supply", *energie—wasserpraxis,* 2010

DVGW working paper G 262 "Use of gases from regenerative sources in the public gas supply grid", November 2004

Energy storage in power supply systems with high percentage of renewable energy sources, Power Engineering Society within VDE, Frankfurt, 2009

Renewable energies in figures—national and international development, Federal Ministry for Environment, Nature Conservancy and Reactor Safety, 2010

George A. Olah et al (2008): Chemical Recycling of Carbon Dioxide to Methanol and Dimethyl Ether, Loker Hydrocarbon Research Institute and Department of Chemistry, University of Southern California, 2008

Guiot et al. (2011): "Potential of wastewater-treating anaerobic granules for biomethanation of synthesis gas", *Environmental Science & Technology* Vol. 45, 2006-2012

Hartmut Wendt (1984): "New design and process engineering concepts for hydrogen production by electrolysis", *Chem. Ing. Tech* 56, 1984

Immhof-Struckle, D. and Pfennig, N. (1983): "Isolation and characterization of a nicotinic acid-degrading sulfate-reducing bacterium, *desulfococcus niacini*". Arch. Microbiol. 136, 194-198

Kopyscinski et al: "Production of synthetic natural gas (SNG) from coal and dry biomass—A technology review from 1950 to 2009", General Energy Research Department, Paul Scherrer Institute, Villingen, Switzerland Klaus, T. et al. (2010): "Energy target 2050: 100% power from renewable sources, Federal Office of Environment, Dessau-RoBlau 2010

Marcus Reppich: "Comparison of different methods of preparation of biogas for feeding to the natural gas grid", Chem. Ing. Tech. 81 No. 3, 2009

Pehnt, Martin; Höpfner Ulrich: Brief report on hydrogen and electricity storage in an energy system with high percentages of renewable energy: analysis of short and medium-term prospects, IFEU—Institut für Energie and Umweltforschung Heidelberg GmbH, commissioned by the Federal Ministry for Environment, Nature Conservancy and Reactor Safety (BMU), Heidelberg, May 2009; Vol. 1.1

Power to Gas: "Investigations in the course of the DVGW Innovation Offensive for energy storage", *energie I wasser-praxis,* 2011

Sahm, H. (1981): "The biology of methane formation", Chem.-Ing. Tech. 53 (11), 854-863

Sahm, H. (1984): "Anaerobic wastewater treatment", *Ad. Biochem. Eng. Biotech.* 29, 83-115

Sahm, H.; Brunner, M.; Schoberth, S. M. (1986): "Anaerobic degradation of halogenated aromatic compounds", *Microbial Ecology* 12, 147-153, Schoberth, S. M., Brunner, M., Sahm, H. (1984): "Anaerobic degradation of 3-chlor-benzoic acid to methane in a defined medium", IAWPRC Symposium on Forest Industry Waste Water, Tamper Schoberth, S. M., Brunner, M., Sahm, H. (1988): "Anaerobic decomposition of halogen aromatics", *Gas-Wasser-Fach* 129, (1), 32-34

Sterner, M. (2009): "Dynamic Simulation of the Electricity Supply in Germany by the Decomposition Scenario of the Renewable Energy Industry, final report, Fraunhofer IWES, 2009

Sterner, M. (2009): "Bioenergy and renewable power methane in integrated 100% renewable energy systems, Limiting global warming by transforming energy systems", dissertation, University of Kassel, Fraunhofer IWES, 2009

Sterner, M.; Specht, M. (2010): "Renewable methane. A solution for the integration and storage of renewable energies and a path to full regenerative supply", In *Solarzeitalter January* 2010

Sterner, M. (2011): "Energy-economic and ecological evaluation of the wind gas supply," Fraunhofer IWES, February 2011

Tom Smolinka et al. (2011): "NOW Study, current state and development potential of water electrolysis for the production of hydrogen from regenerative energies", summary of the final report, 2011

Vereijken, T., Brunner, M. (1989): "New developments in brewery water treatment", *Brauindustrie* June 1989, 653-656

Association of the Swiss Gas Industry (VSG), Agency for Renewable Energies and Energy Efficiency (A EE): "Swiss Renewable Power-to-Gas—Renewable gas from electricity for Switzerland", Bern, June 2012

Widdel, F. (1980): "Anaerobic decomposition of fatty acids and benzoic acid by newly isolated sulfate-reducing bacteria", dissertation, University of Göttingen

The invention claimed is:

1. Device for the production of methane by means of methanogenic microorganisms through conversion of $H_2$ and $CO_2$, having:
    at least one reactor;
    an aqueous medium, which is prepared in the at least one reactor, the methanogenic microorganisms being located in the aqueous medium;
    a feed mechanism, which is designed to channel $H_2$ and $CO_2$ into the at least one reactor, where the $H_2$ and $CO_2$ form a gaseous mixture inside it;
    a driving jet nozzle for generating a driving jet directed into the at least one reactor to increase the contact surface between the aqueous medium with the methanogenic microorganisms and the gaseous mixture;
    a first return pipe fluidly connecting a top end of each of the at least one reactor to the driving jet nozzle to return at least a portion of the gas agglomerating in the reactor to the driving jet nozzle without altering the composition of the returned portion of the gas;
    wherein the return rate of the gas agglomerating in the reactor to the driving jet nozzle is larger than the feed rate of the $H_2$ and $CO_2$ gas into the reactor;
    a second return pipe fluidly connecting a bottom end of each of the at least one reactor to the driving jet nozzle to return at least a portion of the aqueous medium in the at least one reactor to the driving jet nozzle.

2. Device according to claim 1, moreover having:
    a drainage mechanism, which is disposed to drain a gas from the at least one reactor.

3. Device according to claim 2, wherein the gas has methane.

4. Device according to claim 3, wherein a quantitative fraction of methane in the gas is at least 50%.

5. Device according to claim 1, wherein the first return pipe, the second return pipe, or both have a pump or a compressor.

6. Device according to claim 1, moreover having:
    at least one pump, which is disposed to circulate the aqueous medium through the at least one reactor.

7. Device according to claim 6, wherein the pump is a driving jet pump.

8. Device according to claim 1, wherein the device is set up as a stationary or nonstationary reactor.

9. Device according to claim 8, wherein the reactor is a solid state reactor.

10. Device according to claim 1, wherein the device is set up as a submerse reactor.

11. Device according to claim 1, wherein the device is set up as a continuous ideal stirred tank (CSTR), discontinuous ideal stirred tank (STR), tube reactor, loop reactor, reactors switched in series, or a cascade of reactors.

12. Device according to claim 1, moreover having: a reaction boosting device having at least one trickling bed, one spray tower, one in-line mixer or one pump.

13. Device according to claim 12, wherein the pump is a driving jet pump.

14. Device according to claim 1, wherein the feed mechanism has:
    a device for enrichment of carbon dioxide from a gas mixture.

15. Device according to claim 1, wherein the feed mechanism moreover is disposed so that when the $H_2$ and $CO_2$ are channeled into the at least one reactor, the gaseous mixture forms a turbulent flow.

16. Device according to claim 1, wherein the feed mechanism moreover is disposed so that, in operation, the volume of introduced $H_2$ and $CO_2$ per hour is greater than the volume capacity of the at least one reactor by at least a factor of 2.

17. Device according to claim 1, wherein the pressure in the reactor is greater than or equal to 0.1 bar.

18. Device according to claim 1, wherein the methanogenic microorganisms are present in the form of macroscopic colonies in the aqueous medium.

19. Device according to claim 1, wherein the methanogenic microorganisms are not immobilized in the aqueous medium.

* * * * *